(12) United States Patent
Doerr

(10) Patent No.: US 8,014,857 B2
(45) Date of Patent: Sep. 6, 2011

(54) IMPLANTABLE SHOCK ELECTRODE LINE AND IMPLANTABLE DEFIBRILLATION ARRANGEMENT

(75) Inventor: Thomas Doerr, Berlin (DE)

(73) Assignee: Biotronik CRM Patent AG (CH)

( * ) Notice: Subject to any disclaimer, the term of this patent is extended or adjusted under 35 U.S.C. 154(b) by 273 days.

(21) Appl. No.: 12/428,106

(22) Filed: Apr. 22, 2009

(65) Prior Publication Data

US 2009/0292330 A1    Nov. 26, 2009

(30) Foreign Application Priority Data

May 20, 2008   (DE) ................ 10 2008 024 447

(51) Int. Cl.
*A61N 1/05* (2006.01)
(52) U.S. Cl. .......................... 607/3; 607/5; 607/120
(58) Field of Classification Search ............ 607/3–5, 607/7, 119, 120, 122, 123
See application file for complete search history.

(56) References Cited

U.S. PATENT DOCUMENTS

| | | | | |
|---|---|---|---|---|
| 4,360,031 | A * | 11/1982 | White | 607/120 |
| 4,596,575 | A * | 6/1986 | Rosenberg et al. | 604/891.1 |
| 5,325,870 | A * | 7/1994 | Kroll et al. | 607/122 |
| 6,473,653 | B1* | 10/2002 | Schallhorn et al. | 607/116 |
| 6,571,125 | B2* | 5/2003 | Thompson | 604/20 |
| 7,455,667 | B2 | 11/2008 | Uhland et al. | |
| 2003/0032998 | A1* | 2/2003 | Altman | 607/120 |
| 2003/0153951 | A1 | 8/2003 | Ideker | |
| 2006/0041276 | A1 | 2/2006 | Chan | |
| 2006/0047318 | A1* | 3/2006 | Pastore et al. | 607/3 |
| 2007/0150008 | A1 | 6/2007 | Jones et al. | |
| 2008/0033260 | A1 | 2/2008 | Sheppard et al. | |

FOREIGN PATENT DOCUMENTS

| | | |
|---|---|---|
| EP | 1 210 064 B1 | 2/2001 |
| WO | WO 2004/033034 A1 | 4/2004 |
| WO | WO 2004/033036 A2 | 4/2004 |
| WO | WO 2004/071487 A2 | 8/2004 |

OTHER PUBLICATIONS http//www.inm-online.de/pdf/Wissen/Reanimation/algorithmus 2005.pdf.

* cited by examiner

*Primary Examiner* — Carl H Layno
*Assistant Examiner* — Eugene Wu
(74) *Attorney, Agent, or Firm* — Craig A. Fieschko, Esq.; DeWitt Ross & Stevens S.C.

(57) ABSTRACT

An implantable shock electrode line having a proximal terminal for connection to an implantable defibrillator, an elongated flexible line body, and a shock electrode and a drug delivery device arranged at or near the distal end of the line body. A drug depot connected to the drug delivery device is provided in the shock electrode line, and the terminal is designed as a purely electric standard terminal. The drug delivery device is designed for control by an electric pulse transmitted over the electric terminal to the shock electrode line.

20 Claims, 5 Drawing Sheets

IMPLANTABLE SHOCK ELECTRODE LINE AND IMPLANTABLE DEFIBRILLATION ARRANGEMENT

FIELD OF THE INVENTION

The invention relates to an implantable shock electrode line, in particular an endocardial shock electrode line. It also relates to an implantable cardioversion and/or defibrillation arrangement.

BACKGROUND OF THE INVENTION

In addition to implantable pacemaker arrangements, which deliver stimulation pulses to a patient's heart over endocardial electrode lines with distal electrodes, similarly constructed implanted cardioverters or defibrillators have also long been known. These have the important advantage of automatic startup through internal detection of life-threatening cardiac states of the patient, similarly to external defibrillators, which are used by medical personnel when a patient's heart stops. They may thus intervene in a case of ventricular fibrillation or cardiac arrest in a patient with practically no delay and independently of the presence of assistants.

On the other hand, the success rate of implantable cardioverters and/or defibrillators is significantly lower than that of external defibrillators. This is due, firstly, to the limited energy storage capacity of implantable devices with a battery power supply and, secondly, to the restrictions imposed on the electrode line, laid endocardially or epicardially, with regard to the influence of the electric energy of the shock pulses on myocardial tissue.

In addition, today's implantable cardioversion (ICD) systems can be therapeutically successful only when the cause of the ventricular fibrillation (VF) is due strictly to rhythmogenic factors or a temporary disturbance in myocardial profusion. However, sole defibrillation of a VF as part of an acute myocardial infarction tends to have a poor prognosis because after defibrillation, the conditions for renewed VF then still exist unchanged.

Therefore, increasing the defibrillation efficiency has been formulated in expert committees as being an important concern of future ICD therapies. Current ICD systems are fully developed for the most part with regard to the electric therapy and offer only a slight potential for the desired increase in defibrillation efficiency. The anticipated improvements have been very difficult or impossible to detect because of the number of patients required for clinical studies.

In this context, it is noteworthy that in external defibrillation in the context of reanimation, drug therapies are always used in addition to defibrillation, to thereby increase the defibrillation efficiency (see, e.g., http://www.inm-online.de/pdf/Wissen/Reanimation/algorithmus 2005.pdf).

Implantable arrangements for metered delivery of drugs, e.g., in the form of implantable insulin pumps, have long been known and are also in use to a certain extent. Such arrangements have also been the object of intense development efforts in recent years.

For example, EP 1 210 064 B1 presents and claims a thermally activatable microchip as a delivery device for chemicals, in particular drugs, in which the release of the drug from a depot is triggered essentially by resistance heating and subsequent destruction of a cap on the depot. WO 2004/071487 A2 also describes an arrangement for controlled drug delivery, in which a plurality of individual depots is arranged on a substrate, each being openable by electric control to release the quantity of drug contained therein. This also describes how such drug depots are arranged on the distal end of a catheter and are connected to an implantable control unit.

WO 2004/033034 A1 describes a medical device for neural stimulation and controlled drug delivery, also comprising a microchip for drug delivery in addition to an implantable electrode line. The microchip having a plurality of individually controllable drug depots is placed on a device housing which holds a control unit for drug delivery or a joint control unit for drug delivery and electric neural stimulation. WO 2004/033036 A2 describes an arrangement that is very similar but is designed for coordinated drug delivery and cardiac monitoring and/or stimulation. In one embodiment, the arrangement described here also has cardioversion electrodes on corresponding electrode lines, and the drug may also be released from the depots on the device housing with a certain interval of time before delivery of a cardioversion shock pulse.

US 2006/0041276 A1 describes a method and an arrangement for providing combined electrotherapy and drug therapy, which are provided for regulating the cardiac rhythm in particular. In various embodiments, the arrangement comprises an implantable electrostimulation device and implantable drug delivery device combined with a shared electrode catheter or two separate electrode lines and/or infusion lines or an electrostimulation and drug delivery device combined in a single housing and having separate control units or just one shared control unit and a single electrode and drug delivery catheter. It is also described that the implantable medical device may have a cardioversion and/or defibrillation unit and the electrode line and/or the catheter may have shock electrodes.

The approaches known for coordinated electrostimulation (in particular cardioversion/defibrillation) and drug delivery are relatively complex to implement, and are not readily compatible with established ICD approaches.

SUMMARY OF THE INVENTION

The object of the invention is therefore to provide an improved implantable shock electrode arrangement and a corresponding cardioversion/defibrillation arrangement, which can be implemented relatively easily and inexpensively and are compatible with established ICD systems.

This object is achieved by an implantable shock electrode line, and by an implantable cardioversion/defibrillation arrangement, as set forth in the accompanying claims.

In addition to providing the shock pulses, the invention includes the idea of arranging the means required for release of the drug essentially alone in the electrode line in order to be able to form an overall arrangement having possibly improved effects with an essentially known implantable cardioverter/defibrillator. In some versions of the invention, the invention includes the possibility of triggering the drug delivery essentially directly, without additional triggering means, by the output of a cardioversion and/or defibrillation pulse.

The invention increases the prognosis for successful reanimation of a patient through emergency medication of the patient, which is released at the same time as defibrillation. With a suitable dosage, the success rates are assumed to be similar to those with external defibrillation and medication. With ischemia-induced ventricular fibrillation in particular, additional medication may lead to therapeutic success. The electrode used remains compatible with existing ICDs.

The shock electrode line is characterized in that a drug depot is provided in it, and not in the respective defibrillator or in an additional housing. Additionally, the terminal of the electrode line is designed strictly as a standard electric terminal, i.e., not a fluid connection for connection to a drug depot through an external line. The drug delivery device(s) is/are designed for control by electric pulses transmitted to the shock electrode line via the electric terminal, in particular through a pulse that serves as a cardioversion pulse and/or shock pulse.

In one embodiment of the invention, the drug depot is situated at or near the proximal end of the shock electrode line and is connected by a fluid connection to the/each drug delivery device. This makes it possible to accommodate a relatively large amount of the drug, such as that which is typically required for one or more drug-supported defibrillations, and can be accommodated in microcavities of drug dosing chips of the type mentioned above. A suitable dimension of the depot size may be regarded as that sufficient for 10 or more defibrillations or even more specifically for 50 or more defibrillations of a typical course.

The drug depot here is designed in particular as a cohesive cavity on the shock electrode line or in an enlarged area thereof, and is provided with a self-sealing wall for refilling by means of an injection needle in the implanted state. The resulting possibility of refilling the drug depot, optionally even repeatedly, allows long years of use of the defibrillation arrangement even in patients who require relatively frequent defibrillation treatments with drug support.

In another embodiment of the invention, the drug delivery device has a miniature electric pump. In one embodiment of this design, the miniature pump has a piezoelectric drive, and it is preferable to use the energy of a cardioversion and/or defibrillation pulse as the driving energy for the pump.

In another embodiment of the invention, a plurality of drug delivery devices is provided, aligned in a row along the length of the line body. The drug delivery devices are in particular all connected together jointly or at least in groups for simultaneous triggering with the electric terminal of the line (and with the pulse generating unit of the cardioverter and/or defibrillator) and can thereby output a larger drug dose than would be possible with an individual miniaturized device.

Differentiated control of drug delivery that is complementary to the electric pulse action can be performed by having the drug delivery device release the drug on application of a voltage above a certain threshold and/or of a predefined polarity. Depending on the specification for the shock pulse polarity and/or energy, a drug may be administered with the shock pulse, or may be avoided with delivery of the shock pulse. With the availability of shock pulse sequences programmed in a predetermined manner with an increasing voltage level and/or with a changing polarity, one portion of the electric cardioversion therapy may be performed without delivery of a drug, while another portion is performed with the delivery of a drug.

In another version, at least two separate drug depots are provided in the shock electrode line, and drug delivery devices that respond to different electric triggering —in particular to different voltage levels or different polarities of a shock pulse—are provided in connection to the separate drug depots. This makes it possible to store different cardioversion supporting drugs in the electrode line and also to deliver them to the patient in different ways as a function of the essential parameters of the cardioversion and/or defibrillation pulses to be output. In conjunction with a suitable sensor system of the defibrillator (which is known per se and therefore needs no further description here), differentiated treatment courses with different drug doses can therefore be controlled in this way.

Another possibility for flexible control of drug delivery is by providing means for blocking the drug delivery device(s) for inhibition of a drug delivery. These means may have a control line for connection to the defibrillator and/or a reed switch for operation from outside of the body. Reed switches, as special magnetic switches of implantable devices for operation from outside of the body, are essentially known and commercially available, so no further detailed description is necessary in this regard.

In contrast with some other arrangements described above having a drug dosing chip mounted on the device body, the implantable defibrillation arrangement of the invention is characterized in that drug delivery devices are provided in the shock electrode line. The drug supporting the electrostimulation can therefore also be administered directly at the site of delivery of the electric pulses, while at the same time preventing inefficient drug delivery at an inappropriate location in the body.

With regard to the long-established and largely standardized ICD systems, it is advantageous that the inventive arrangement has a standard defibrillator which has an output for delivery of shock pulses but does not have an additional control output. According to an especially appropriate design from the standpoint of existing standards, the terminal for the connection between the shock electrode line and the defibrillator is designed as a terminal according to the IS-1/DF-1 or IS-4 standards.

BRIEF DESCRIPTION OF THE DRAWINGS

Advantages and useful features of the invention are also set forth in the following description of exemplary versions of the invention, with reference to the figures wherein.

DETAILED DESCRIPTION OF THE INVENTION

Figure 1:
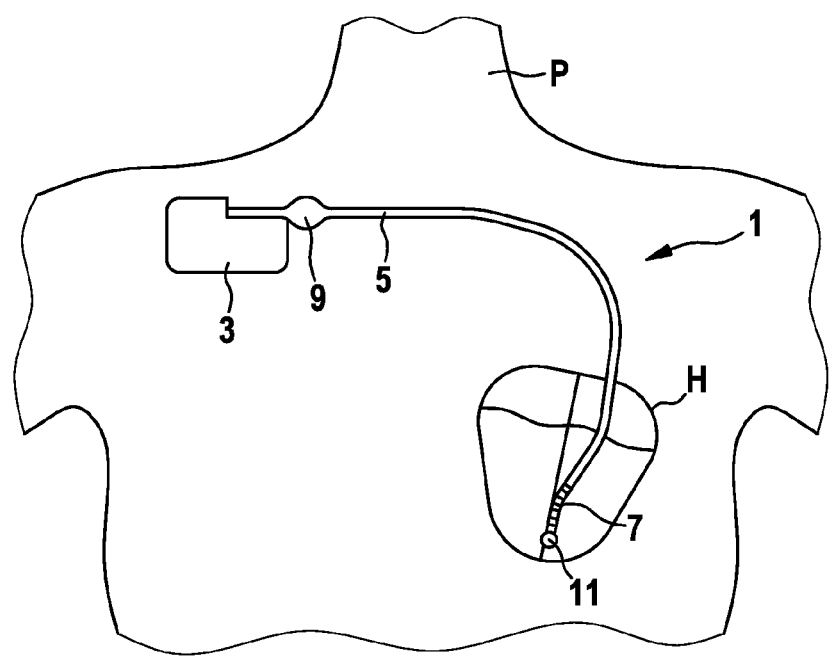
FIG. 1 shows a schematic diagram of an exemplary implantable inventive defibrillation arrangement.

FIG. 1 shows an implantable defibrillation arrangement 1 with an implanted defibrillator (power supply and control unit) 3 and a shock electrode line 5 connected to it, its distal end being placed in the heart H of a patient P and having a shock electrode segment 7 in contact with the wall of the patient's heart. A drug depot 9 is arranged near the proximal end of the electrode line 5, and a drug delivery device 11 is provided at the distal end. The electrode line thereby gains the combined properties of an electric defibrillation line and a catheter for defibrillation with supportive drug delivery.

Figure 2:
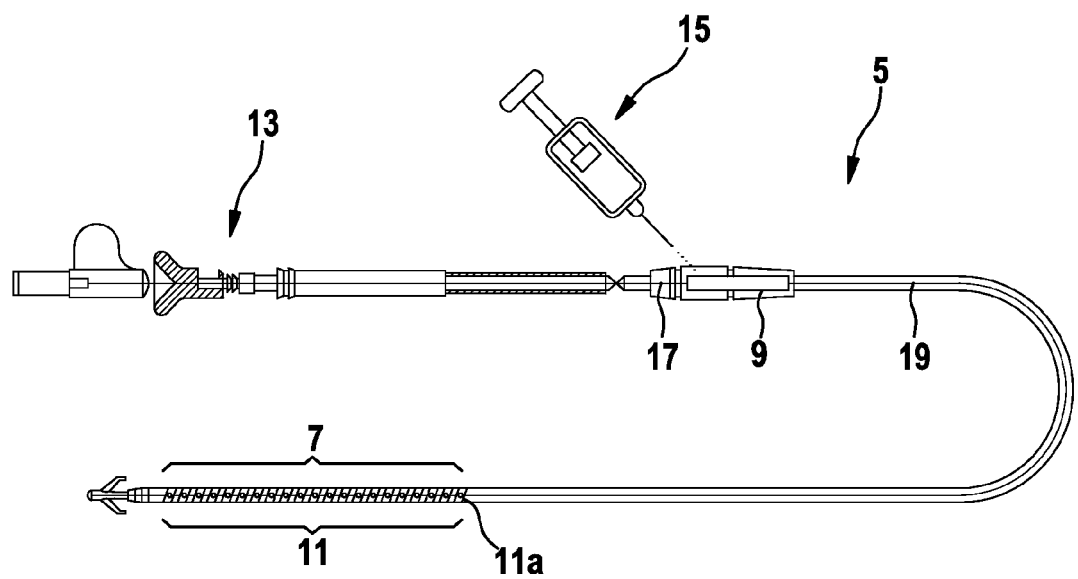
FIG. 2 shows a schematic diagram of a shock electrode line before implantation, including the insertion connector and guide wire.

In somewhat greater detail, FIG. 2 shows such a line 5 in the startup phase of an implantation process, i.e., in combination with an insertion connector 13, as well as in combination with an infusion syringe 15 for refilling the drug depot 9. In addition to the guide wire 17 (which is present only during the implantation process), a fluid connection (a drug channel)

19 runs in the longitudinal direction of the line between the drug depot 9 and the drug delivery device 11, comprising multiple miniature pumps 11a which are here provided near the distal end of the line. As shown by the symbolic representation of the infusion syringe 15, the drug depot 9 here is designed to be refillable, i.e., it is provided with a wall that is self-sealing after being punctured and preferably has a suitable X-ray marker (not shown) to facilitate refilling with radiological observation.

Figure 3:
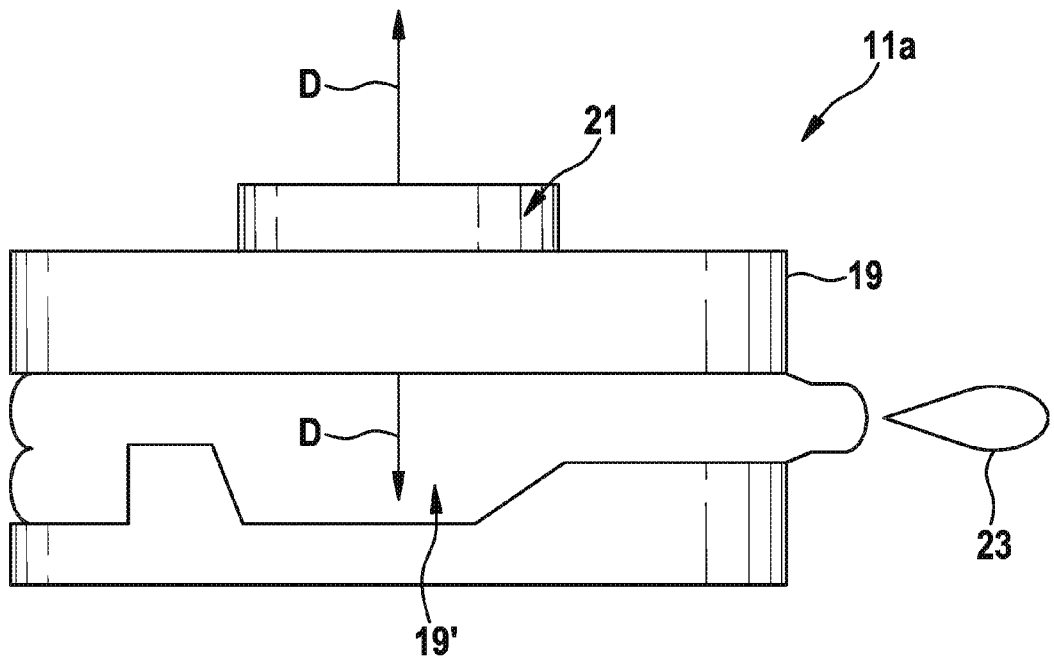
FIG. 3 shows a schematic diagram of a piezoelectric drug pump usable in the shock electrode line.

As an example of a miniature pump 11a, FIG. 3 shows schematically a pump that operates on a piezoelectric basis. A piezoelectric crystal 21, which can be excited by electrodes at the end (not shown) to undergo deformation D sits here on a pump body 19. As a result of deformation, symbolized by arrows in the figure, the wall of a segment 19' of the drug channel provided in the pump body 19 is pressed inward. As a result of this process, one droplet of drug 23 is expressed out of the channel segment 19'.

It should be pointed out that the diagram in FIG. 3 is highly schematic and cannot fully show the actual design of a miniature piezoelectric pump. Such pumps have been in industrial use for a long time, e.g., in inkjet printers, and therefore need not be described in greater detail here. It should also be pointed out that arrays of multiple miniature pumps aligned in rows are also known (again in inkjet pumps, for example) and may also be used to implement the present invention.

The piezoelectric element 21 may be electrically wired such that one pole is connected directly to the shock electrode 7, but the other pole is connected to a reference potential (e.g., on the ring electrode of the electrode line). In this way, the miniature pump 11a is driven directly by the shock energy of a cardioversion and/or defibrillation process and it is advantageous that no separate drive and no special control are needed.

Figure 4:
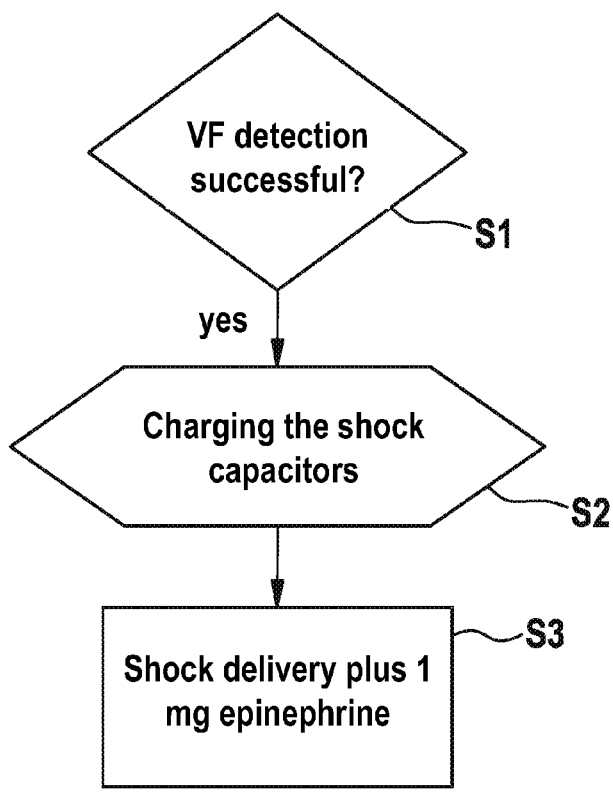
FIG. 4 shows a simplified flow chart of the operation of an exemplary version of the invention.

FIG. 4 shows schematically how a combined electric defibrillation and drug dosing process proceeds with an arrangement of the type illustrated in FIG. 1. First, in a step S1, a sensor in the heart detects when a ventricular fibrillation (VF) occurs. If this is the case, then in a step S2, shock capacitors of the defibrillator 3 are charged, and after the end of the charging, in a step S3 a defibrillation pulse is output and the delivery of a predetermined drug dose (e.g., 1 mg epinephrine) is performed via the drug delivery device(s) through this pulse at the same time.

Figure 5:
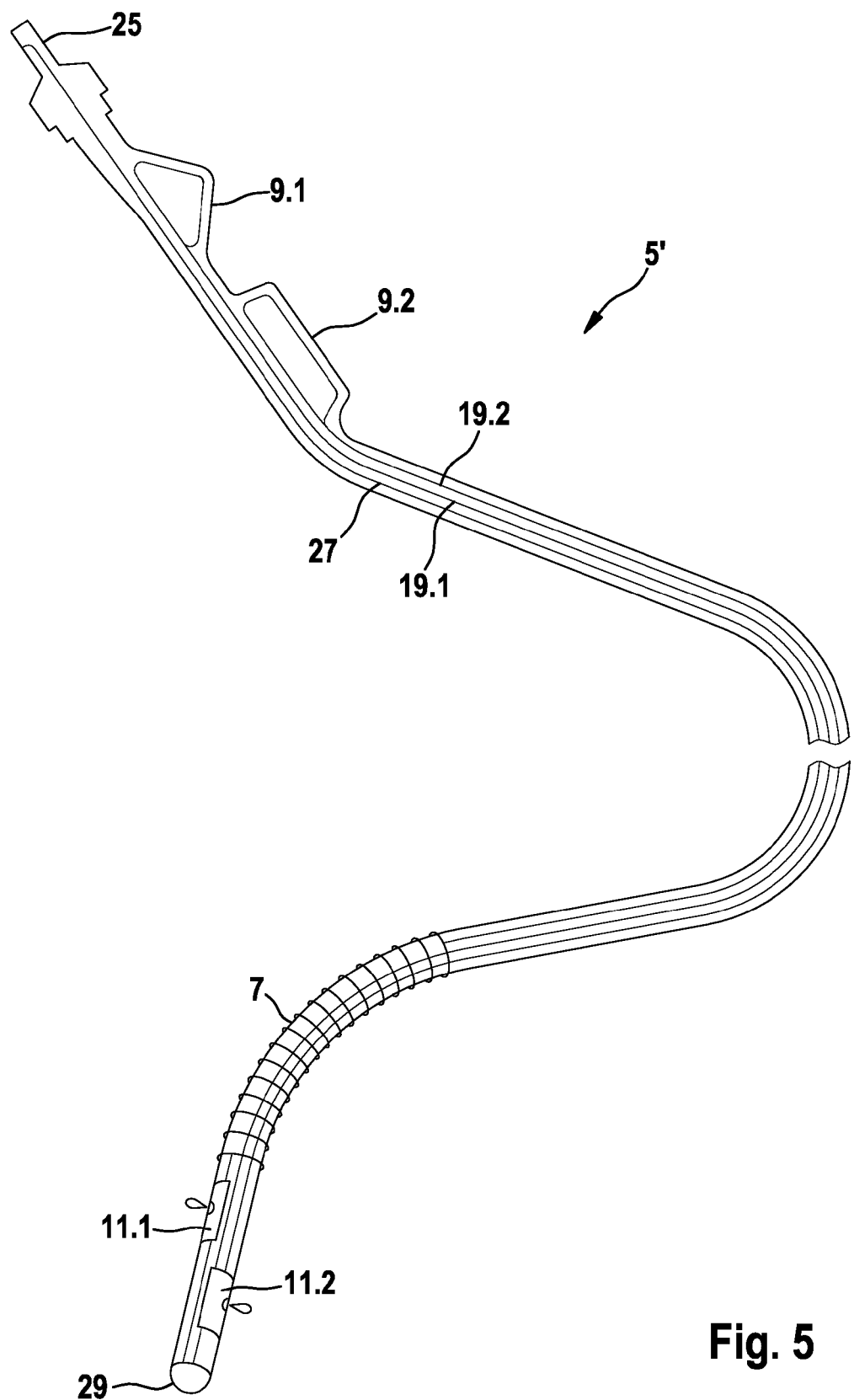
FIG. 5 shows a schematic diagram of a shock electrode line exemplifying another version of the invention.

Differentiated drug support of cardioversion attempts is possible with a shock electrode line 5' such as that diagrammed schematically in FIG. 5. Near the proximal end (e.g., near an electric terminal plug 25, which is usually provided there), first and second drug depots 9.1, 9.2 are provided, in order to be able to supply two different cardioversion supporting drugs. In their external form, the two drug depots 9.1, 9.2 are folded, so that they are palpable for refilling by means of an infusion syringe and/or can be differentiated with no confusion in an X-ray.

In addition to an electrode feeder line 27 (shown here as an elongated wire in simplified form, but typically in the form of a coil in the practical embodiment), a pair of thin fluid lines 19.1, 19.2 run along the line body, connecting the first and second drug depots 9.1, 9.2 to first and second drug pumps 11.1, 11.2 on the distal end of the line 5'. The electrode feeder line 27 connects the plug 25 to the shock electrode 7 and the electrode 7 is in turn connected to terminals of the two pumps 11.1 and 11.2 (which can be represented only symbolically in the figure). A tip electrode 29 of the line 5' may serve to pick up heart action potentials and may thus be used to detect a ventricular fibrillation requiring treatment but is also connected to the reference potential terminals of the pumps 11.1 and 11.2 (the required line connection to the plug 25 has been omitted from the figure for reasons of a simple overview).

Figure 6:
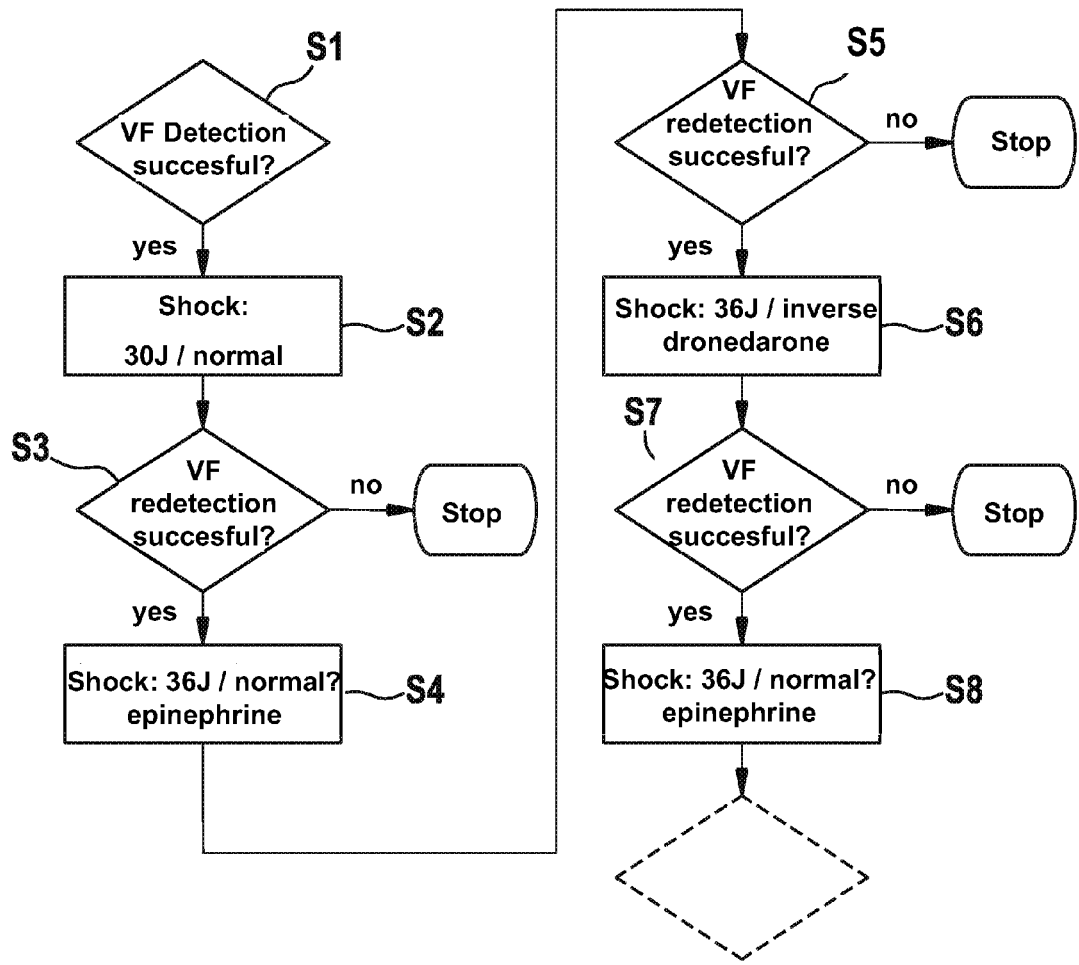
FIG. 6 shows a flow chart of operation of a defibrillation arrangement comprising a shock electrode line according to FIG. 5, and FIGS. 7a and 7b show schematic detailed diagrams of two variants of another version of the inventive shock electrode line.

The function of the electrode line shown in FIG. 5 is described in combination with the flow chart for a multi-step defibrillation process as shown in FIG. 6.

The flow chart shown in FIG. 6 illustrates an exemplary multi-step concomitant drug therapy according to the current guidelines for reanimation in automatic defibrillation. First there is VF detection (S1) and defibrillation with a shock energy lower than the maximum shock energy (S2) without concomitant medication. If this is unsuccessful, which is ascertained in a step S3, defibrillation is performed again at the maximum energy, with the normal shock polarity and simultaneous intracardiac administration of epinephrine (S4). If this treatment is also unsuccessful, as ascertained in a step S5, the next shock is delivered at the maximum shock energy (S6), but this time with the inverse shock polarity and intracardiac administration of dronedarone (or alternatively amiodarone). In a detection step S7, the result is again checked here, and if unsuccessful, up to three additional maximum energy shocks of a normal polarity are delivered with administration of epinephrine (S8).

In this exemplary embodiment, the drug pump is controlled via the shock energy and shock polarity. The drug pump is supplemented here by a trigger unit, which depends on polarity and voltage, so that epinephrine is administered at the maximum shock energy and normal polarity and dronedarone is administered at maximum shock energy and inverse polarity. If the shock energy is lower than the maximum energy, no drug is delivered.

Figure 7A:
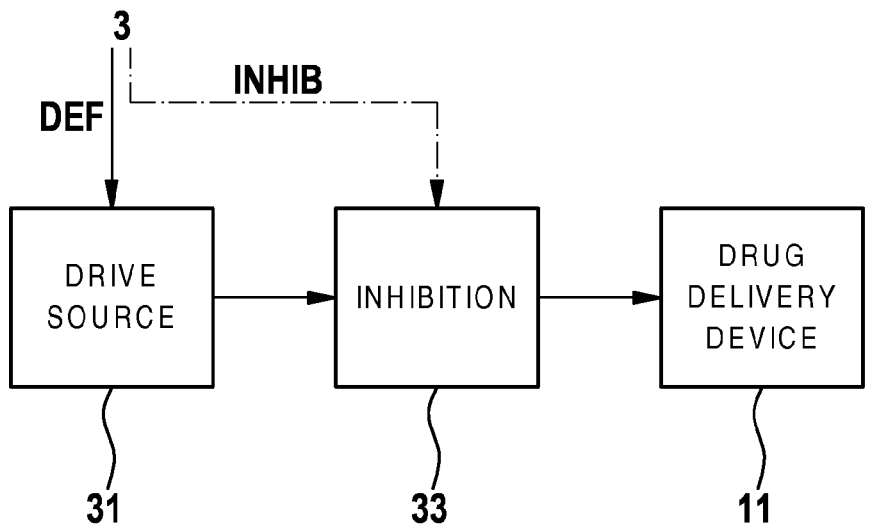
Figure 7B:
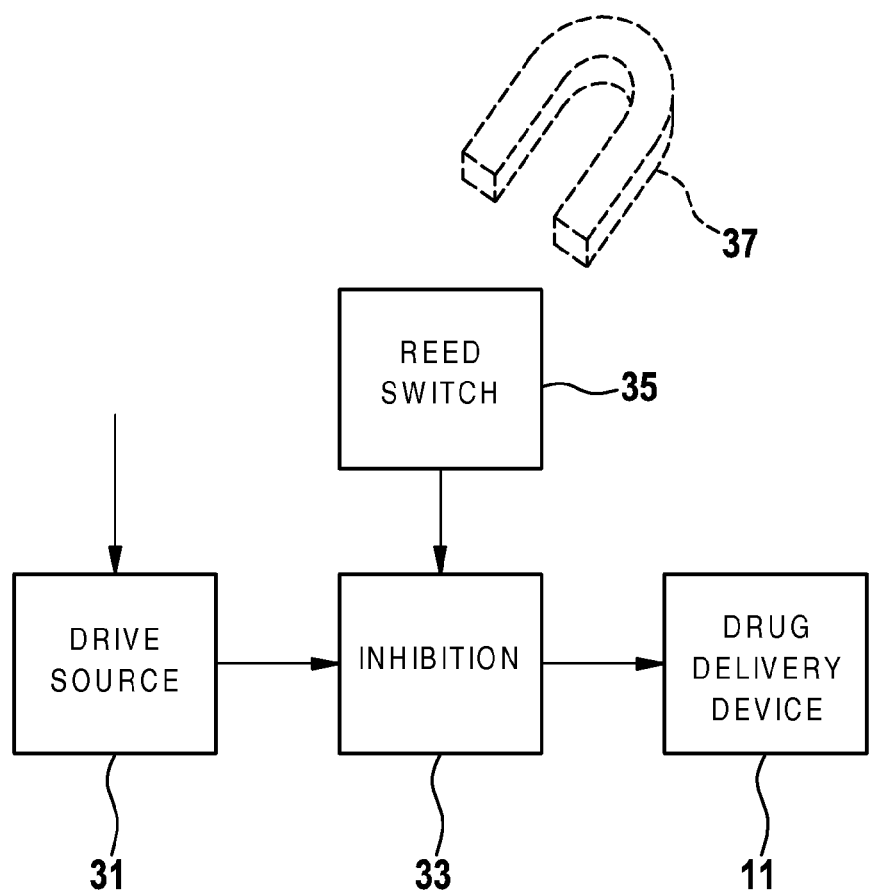

FIGS. 7a and 7b show schematically in the manner of a function block diagram two possibilities for optional inhibition of a drug delivery in a cardioversion and/or defibrillation process. With the two configurations illustrated here, an inhibition step 33 is connected between a drug delivery device 11 and a respective drive source 31, which in turn receives a control signal DEF from the cardioverter/defibrillator belonging to the configuration. The arrangement according to FIG. 7a receives a control signal INHIB from the defibrillator 3 in the inhibition case and triggers activation of the inhibition step and thus suppression of the connection between the drive and the drug delivery device. In the embodiment according to FIG. 7b, this is accomplished by a reed contact 35, which can be operated by a magnet 37 from outside of the body.

The invention is not limited to the examples described above, and can be provided in a variety of other forms as set forth in the claims below.

What is claimed is:

1. An implantable shock electrode line including an elongated line body extending between:
   a. a proximal end bearing:
      (1) an electric terminal, and
      (2) a drug depot;
   b. a distal end bearing:
      (1) a shock electrode, the shock electrode being configured to deliver a shock upon receipt of an electric pulse transmitted from the electric terminal, and
      (2) a drug delivery device including one or more piezoelectrically-driven pumps, the drug delivery device being configured to deliver a dose of a drug from the drug depot when the electric pulse is transmitted from the electric terminal to the shock electrode.

2. The shock electrode line of claim 1 wherein the terminal lacks any fluid conduits in communication with the drug delivery device.

3. The shock electrode line of claim 1 wherein two or more drug delivery devices are:

a. spaced along the distal end of the line body, and
　　b. configured to be triggered by pulses transmitted from the electric terminal which have different electrical qualities.

4. An implantable shock electrode line including:
　a. an electric terminal,
　b. an elongated line body extending from the electric terminal at a proximal line body end, and
　c. a shock electrode at or near a distal line body end opposite the proximal line body end,
　d. an electrically-actuated pump on the line body at or near the shock electrode,
　e. a drug depot at or near the proximal line body end, the drug depot being connected to the pump via a fluid connection,
　wherein the pump is configured to be triggered by an electric pulse transmitted from the electric terminal to the shock electrode.

5. An implantable shock electrode line including:
　a. an elongated flexible line body extending between a proximal end and a distal end,
　b. an electric terminal for connection to an implantable defibrillator at the proximal end,
　c. a shock electrode at the distal end, and
　d. a drug delivery device at the distal end, wherein the drug delivery device is configured to be triggered by an electric pulse transmitted from the electric terminal to the shock electrode.

6. The shock electrode line of claim 5 further including a drug depot:
　a. at or near the proximal end, and
　b. connected to the drug delivery device via a fluid connection.

7. The shock electrode line of claim 5 wherein the terminal lacks any fluid conduits.

8. The shock electrode line of claim 5 further including a drug depot:
　a. being situated along the line body,
　b. connected to the drug delivery device via a fluid connection, and
　c. having a self-sealing wall configured to be refilled by means of an inserted injection needle.

9. The shock electrode line of claim 5 wherein the drug delivery device includes an electrically actuated pump.

10. The shock electrode line of claim 9 wherein the pump:
　a. has a piezoelectric drive, and
　b. is configured to be electrically actuated by an electric pulse transmitted from the electric terminal to the shock electrode.

11. The shock electrode line of claim 5 including two or more drug delivery devices situated along the line body.

12. The shock electrode line of claim 11 wherein the drug delivery devices are all:
　a. connected in communication with the electric terminal, and
　b. configured to be electrically actuated by an electric pulse transmitted from the electric terminal to the shock electrode.

13. The shock electrode line of claim 5 wherein:
　a. two or more drug delivery devices are:
　　(1) spaced along the line body,
　　(2) each in fluid communication with a respective drug depot, and
　　(3) configured to be triggered by a pulse transmitted from the electric terminal, and
　b. the different drug depots are configured to eject one or more of:
　　(1) different drugs, and
　　(2) different doses of drug.

14. The shock electrode line of claim 5 wherein the drug delivery device is configured to be triggered to release a drug only upon receipt of at least one of:
　a. a voltage above a certain threshold level, and
　b. a voltage of a certain polarity.

15. The shock electrode line of claim 5 including first and second drug delivery devices wherein:
　a. the first drug delivery device is configured to be triggered to release a drug upon receipt of a first electrical signal, and
　b. the second drug delivery device is configured to be triggered to release a drug upon receipt of a second electrical signal,
　wherein the first and second electrical signals differ in their electrical qualities.

16. The shock electrode line of claim 15 wherein the first and second electrical signals differ in one or more of:
　a. voltage, and
　b. polarity.

17. The shock electrode line of claim 5:
　a. wherein the drug delivery device is configured to eject a set dose of a drug when triggered, and
　b. further including a drug depot connected to the drug delivery device, wherein the drug depot holds several set doses of the drug.

18. The shock electrode line of claim 5:
　a. including two or more drug delivery devices, each being configured to be electrically actuated by an electric pulse transmitted from the electric terminal to the shock electrode, and
　b. one or more of the drug delivery devices are configured to be selectively blockable whereby their actuation is prevented during transmission of the electric pulse from the electric terminal to the shock electrode.

19. The shock electrode line of claim 18 wherein one or more of the drug delivery devices are configured to be selectively blockable by a signal from a control line extending from the electrical terminal.

20. The shock electrode line of claim 18 wherein one or more of the drug delivery devices are configured to be selectively blockable by a magnetically-actuated switch.

* * * * *